United States Patent [19]

Archer

[11] Patent Number: 4,502,337

[45] Date of Patent: Mar. 5, 1985

[54] FATIGUE DAMAGE INDICATOR

[75] Inventor: Michel Archer, La Celle-St. Cloud, France

[73] Assignee: Societe Anonyme S.T.A.S. Societe Technique d'Accessoires Specialises, Sartrouville, France

[21] Appl. No.: 480,403

[22] Filed: Mar. 30, 1983

[30] Foreign Application Priority Data

Mar. 30, 1982 [FR] France .................................. 82 05833

[51] Int. Cl.³ .............................................. G01N 19/08
[52] U.S. Cl. ......................................... 73/762; 73/787
[58] Field of Search ................. 73/762, 799, 775, 786, 73/787

[56] References Cited

U.S. PATENT DOCUMENTS 4,409,841 10/1983 Archer .................................. 73/762

Primary Examiner—Anthony V. Ciarlante
Attorney, Agent, or Firm—Karl F. Ross; Herbert Dubno

[57] ABSTRACT

The present invention relates to an improved fatigue damage indicator for a mechanical member subjected to repetitive stress, comprising two thick elements which are spaced from one another and are connected one to the other by a thin web or plate formed with a slot and at least one pair of free opposite edges, the two elements being so connected with the mechanical member or fixed to the latter so that they are displaceable relative to one another in a plane parallel to the plane of the thin plate, the thick elements being disposed so as to be separated from one another in a direction substantially perpendicular to their direction of relative displacement by such stress, the thin plate being placed under shear force in its plane by such relative displacement, the slot of the thin plate extending from one of the edges of the web in the said direction and terminating short of the opposite edge in a blind end of the slot having two corners so that, with application of stress, two cracks develop at corners of the bottom of the crack and are propagated progressively in the web towards an opposite edge of the thin plate so that said cracks meet cracks propagating generally in a direction away from said opposite edge to detach, or substantially detach, a central zone of the thin plate delimited by said cracks, wherein the thick elements of the fatigue damage indicator are connected to each other not only by thin webs but in addition by two narrow, elongated struts disposed on either side of the web and directed perpendicularly to the axis of one or the two slots in this web.

4 Claims, 2 Drawing Figures

FATIGUE DAMAGE INDICATOR

CROSS REFERENCE TO RELATED APPLICATION

This application is related to my copending application Ser. No. 221,212 filed Dec. 30, 1983, U.S. Pat. No. 4,409,841.

FIELD OF THE INVENTION

This invention relates to a fatigue damage indicator.

BACKGROUND OF THE INVENTION

In my patent application Ser. No. 221,212, now U.S. Pat. No. 4,409,841 I have described a fatigue damage indicator for a mechanical member subjected to repetitive stress, comprising two thick elements which are spaced from one another and are connected one to the other by a thin plate formed with a slot and at least one pair of free opposite edges, the two elements being so connected with the mechanical member or fixed to the latter so that they are displaceable relative to one another in a plane parallel to the plane of the thin plate.

My fatigue damage indicator is characterized in that the thick elements are disposed so as to be separated from one another in a direction substantially perpendicular to their direction of relative displacement by such stress, the thin plate being placed under shear force in its plane by such relative displacement, the slot of the thin plate extending from one of the edges of the web in the said direction and terminating short of the opposite edge in a blind end of the slot having two corners so that, with application of stress, two cracks develop at corners of the bottom of the crack and are propagated progressively in the web towards an opposite edge of the thin plate so that said cracks meet cracks propagating generally in a direction away from said opposite edge to detach or substantially detach a central zone of the thin plate delimited by said cracks.

This fatigue damage indicator is essentially intended to indicate the fatigue of a piece subjected to tensile or compressive stresses.

However, in practice, a piece is not subjected to a pure tensile or compressive force; often, it is also subjected to a shear stress or to torsional or bending moments. Such parasitic stresses and moments influence the functioning of the fatigue damage indicator and it so happens that, in practice, the web is detached for a fatigue different from that for which the indicator has been calibrated.

OBJECT OF THE INVENTION

My invention has for its object to provide an indicator of the above-described type which remedies this drawback.

SUMMARY OF THE INVENTION

According to the present invention, the thick elements of the indicator are connected to one another not only by thin webs but, in addition, by two narrow, elongated struts disposed on either side of the web and directed perpendicularly to the axis of the or each slot of this web.

In an advantageous embodiment of the invention, the assembly formed by the web and the thick parts with their struts is connected by flexible zones to the part for fixation on the piece to be monitored.

These flexible zones enable the indicator to undergo the bending or torsional deformations of the piece without these deformations influencing the web.

These flexible zones may be constituted by narrow bridges arranged transversely beyond the struts, in the same plate forming both the indicator and its parts for fixation on the piece to be monitored.

It is advantageous to dispose on the same piece to be monitored several fatigue damage indicators calibrated for different fatigues. It is thus possible for the user to monitor the development of fatigue in the piece in time. In that case, the fatigue damage indicator assembly may be constituted by two or more thin webs connecting two similar thick elements to each other. It is then advantageous if the thick elements are connected to each other by flexible parts disposed between the adjacent webs. These bridges avoid the influence on the webs of the stresses which may exist due to the length of the assembly of the thick elements.

BRIEF DESCRIPTION OF THE DRAWING

Two embodiments of a fatigue damage indicator improved according to the invention will be described hereinafter by way of non-limiting example, with reference to the accompanying drawing, in which.

SPECIFIC DESCRIPTION

Figure 1:
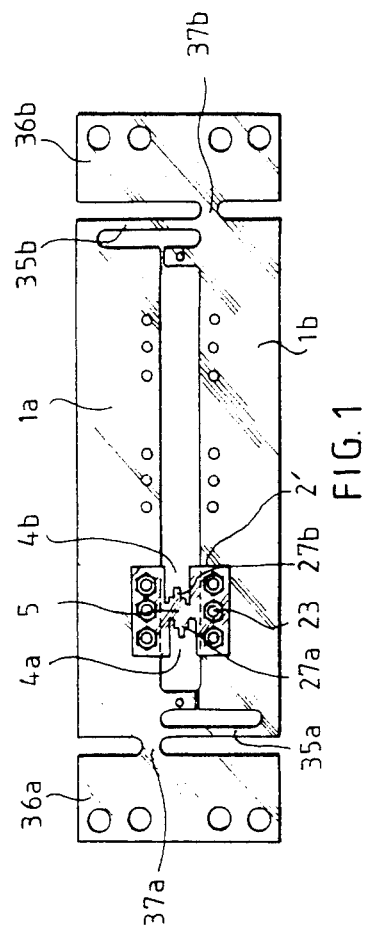
FIG. 1 is a plan view of a first embodiment of the fatigue damage indicator.

Referring now to the drawings, FIG. 1 shows the thin web or plate 2' which is independent of the thick parts 1a and 1b and fixed thereto by bolts 23. The web is of the type shown in FIG. 24 of my prior Patent Application, i.e. the bottom of each of the slots 4a and 4b comprises a tab 27a or 27b which is raised outside the plane of the thin web 2', one on one side of this plane and the other on the opposite side. Each of these tabs serves to hook one of the ends of a spring (not shown) of which the other end is fixed either to the piece whose fatigue is to be monitored, or to two points of the web 2'.

The springs 28 exert a moment on the central part 5 located between the slots 4a and 4b. When the piece is fatigued and cracks starting from the corners of the slots are on the point of meeting two by two, the moment causes the central part 5 to pivot. If the material of which the web is composed is hardly ductile, there is rupture at the ends of the cracks and the central part 5 is automatically ejected. If the material is more ductile, it may be that part 5 remains attached to the two points of the web 2', but its pivoting indicates that the piece is fatigued.

However, the two thick parts 1a and 1b, instead of being connected to each other solely by the thin web 2', are in addition connected to each other by two narrow, elongated struts 35a and 35b which are directed perpendicularly to the direction of displacement of parts 1a and 1b, i.e. to the longitudinal axis of parts 4a and 4b.

Furthermore, the assembly formed by the web 2' and the thick parts 1a and 1b with their struts 35a and 35b is extended longitudinally by parts 36a and 36b by which the fatigue damage indicator may be fixed on the piece to be monitored. These fixing parts are connected to said assembly by narrow bridges 37a and 37b made transversely beyond the struts 35a and 35b and which constitute flexible zones.

When the piece to be monitored is subjected to a tensile or compressive stress, this stress is transmitted by the bridges 37a and 37b to the thick parts 1a and 1b.

The thick parts may move longitudinally with respect to each other since, during this movement, the struts bend. The web 2' is thus subjected to the shear stress in its fatigue damage indicator. However, the piece to be monitored is moreover subjected to a shear stress which tends to displace the two fixing parts 36a and 36b with respect to each other in the direction of the struts; the latter which are then subjected to a compressive or tensile force absorb all the stress which is thus not transmitted to web 2'.

If the piece to be monitored is subjected to a parasitic moment, the latter has only a minimum value with respect to the tensile or compressive stress. In the case of a torsional moment, the bridges 37a and 37b which constitute sites of least resistance become twisted, preventing the transmission of this moment to the web 2'. In the case of a bending moment, the bridges 37a and 37b bend, and, there again, the moment is not transmitted to the web 2'.

It is thus seen that, if the piece to be monitored is not subjected to this pure tensile or compressive stress, the parasitic stresses or moments have virtually no effect on the shear stress to which the web 2' is subjected and therefore do not influence the indications given by the fatigue damage indicator.

In the embodiment shown in FIG. 1, the thick parts 1a and 1b are connected to each other by three webs, only one of which is shown and of which each constitutes a fatigue damage indicator. The webs are arranged so that their central zone 5 detaches for different fatigues. The user may thus monitor the development of the fatigue of the piece in time.

Figure 2:
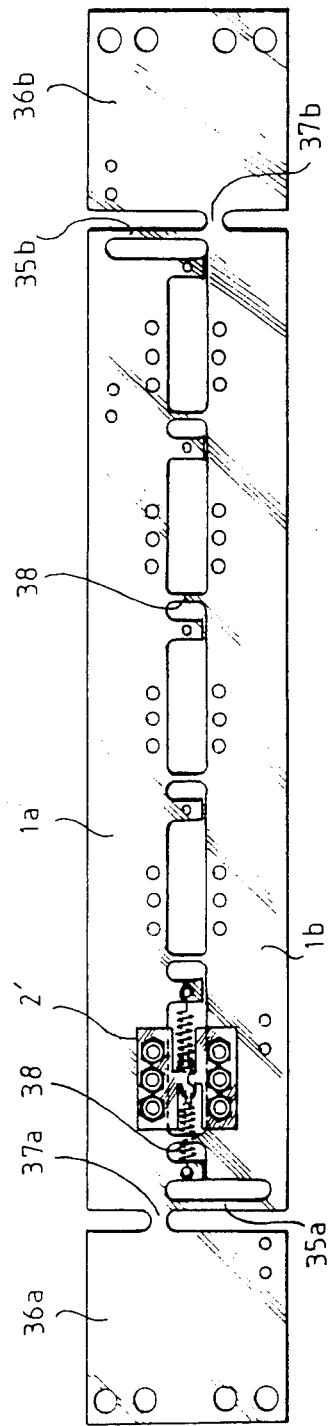
FIG. 2 is a plan view of a second embodiment of this indicator.

The embodiment of FIG. 2 is basically similar to that of FIG. 1, particularly in that it comprises a plurality of fatigue damage indicators each formed by a web 2' fixed on the same thick parts 1a and 1b. However, parts 1a and 1b are connected to each other not only by the struts 35a and 35b but also by flexible bridges 38 disposed between two adjacent fatigue damage indicators. These bridges prevent the parasitic influences due to the length of parts 1a and 1b.

It goes without saying that the present invention is not to be considered as being limited to the embodiments described and shown, but covers, on the contrary, all the variants thereto.

What is claimed is:

1. In a fatigue damage indicator for a mechanical member subjected to repetitive stress, comprising two thick elements which are spaced from one another and are connected one to the other by a thin plate formed with a slot and at least one pair of free opposite edges, the two elements being so connected with the mechanical member or fixed to the latter so that they are displaceable relative to one another in a plane parallel to the plane of the thin plate, the thick elements being disposed so as to be separated from one another in a direction substantially perpendicular to their direction of relative displacement by such stress, the thin plate being placed under shear force in its plane by such relative displacement, the slot of the thin plate extending from one of the edges of the thin plate in the said direction and terminating short of the opposite edge in a blind end of the slot having two corners so that, with application of stress, two cracks develop at corners of the bottom of the crack and are propagated progressively in the thin plate towards an opposite edge of the thin plate so that said cracks meet cracks propagating generally in a direction away from said opposite edge to detach, or substantially detach, a central zone of the thin plate delimited by said cracks, the improvement wherein the thick elements of the fatigue damage indicator are connected to each other not only by said thin plate but in addition by two narrow, elongated struts disposed on either side of the thin plate and directed perpendicularly to the axis of one or the two slots in this thin plate.

2. The improvement defined in claim 1, wherein the assembly formed by the thin plate and the thick parts with their struts is connected by flexible zones to parts for fixation to the piece to be monitored.

3. The improvement defined in claim 2, wherein the flexible zones are constituted by narrow bridges arranged transversely beyond the struts, in the same plate forming both the thick parts of the indicator and its parts for fixation on the piece to be monitored.

4. In a fatigue damage indicator for a mechanical member subjected to repetitive stress, comprising two parallel elongated thick elements which are spaced from one another and are connected one to the other by thin plate formed with a slot and at least one pair of free opposite edges, the two elements being so connected with the mechanical member or fixed to the latter so that they are displaceable relative to one another in a plane parallel to the plane of the thin plate, the thick elements being disposed so as to be separated from one another in a direction substantially perpendicular to their direction of relative displacement by such stress, the thin plate being placed under shear force in its plane by such relative displacement, the slot of the thin plate extending from one of the edges of the thin plate in the said direction and terminating short of the opposite edge in a blind end of the slot having two corners so that, with application of stress, two cracks develop at corners of the bottom of the crack and are propagated progressively in the web towards an opposite edge of the thin plate so that said cracks meet cracks propagating generally in a direction away from said opposite edge to detach or substantially detach a central zone of the thin plate delimited by said cracks, the improvement wherein the said indicator comprises two or more thin plates connecting two similar thick elements to each other, the elements being connected to one another by flexible bridges disposed between adjacent thin plates and independent thereof.

* * * * *